United States

Taylor et al.

4,006,251

Feb. 1, 1977

[54] BACTERICIDAL AND FUNGICIDAL COMPOSITION CONTAINING THIOCARBANYL SULFENAMIDES

[75] Inventors: Ray D. Taylor, Brecksville; Robert A. Krueger, Cuyahoga Falls, both of Ohio

[73] Assignee: The B. F. Goodrich Company, Akron, Ohio

[22] Filed: July 9, 1973

[21] Appl. No.: 377,419

[52] U.S. Cl. .............................. 424/328; 106/15 R; 260/246 B; 260/247.1 R; 260/247.1 T; 260/567; 424/248.5; 424/286

[51] Int. Cl.² ...................................... A01N 9/20

[58] Field of Search ......... 424/298, 300, 286, 320, 424/328; 260/455 A

[56] References Cited

UNITED STATES PATENTS

| | | | |
|---|---|---|---|
| 2,333,468 | 11/1943 | Cooper ........................ 260/455 A |
| 2,390,713 | 12/1945 | Hunt .......................... 260/455 A X |
| 2,395,440 | 2/1946 | Ainley et al. ............... 260/455 A X |
| 2,432,256 | 12/1947 | Skaptason ...................... 424/320 |
| 2,598,989 | 6/1952 | Goodhue et al. ............. 424/286 X |
| 2,650,876 | 9/1953 | Stewart ...................... 260/455 A X |
| 2,692,862 | 10/1954 | Lipsitz ......................... 424/300 X |
| 2,792,394 | 5/1957 | Himel et al. ............... 260/455 A X |
| 3,883,592 | 5/1975 | Gattuso et al. ................. 260/567 |
| R22,750 | 4/1946 | Tisdale et al. ................ 260/455 A |

OTHER PUBLICATIONS

Smith, J. Org. Chem., 1949, vol. 14, pp. 935–945.
Kempermann, Anwendungstechnische Abteilung der Farbenfabriken, 1/12/1967, pp. 126–134.

*Primary Examiner*—Dale R. Ore
*Attorney, Agent, or Firm*—Alan A. Csontos

[57] ABSTRACT

Thiocarbamylsulfenamide compounds having alicyclic or heterocyclic groups are good fungicides and bactericides. The compounds exhibit good stability during storage, and are useful to prepare disinfectant compositions.

4 Claims, No Drawings

BACTERICIDAL AND FUNGICIDAL COMPOSITION CONTAINING THIOCARBANYL SULFENAMIDES

BACKGROUND OF THE INVENTION

Compounds having anti-bacterial and/or anti-fungal properties are used in disinfectant formulations to kill and arrest the growth of infectious organisms. Certain compounds containing a thiocarbamylthio structure are known to have fungicidal and bactericidal properties (See U.S. Pat. Nos. 2,692,862; 2,432,256 and Re 22,750). However, compounds having these properties are highly specific in their application. Furthermore, activity towards a given organism(s) is but one factor to consider in the successful use of a compound in a disinfectant formulation. Compounds having a broad range of activity towards organisms and good storge stability, without having toxic effects are highly desirable.

SUMMARY OF THE INVENTION

Compositions containing thiocarbamylsulfenamides of the formula

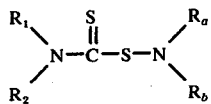

wherein the compound is selected from the group consisting of (1) compounds wherein $R_1$ and $R_2$ are alkyl radicals containing 1 to 3 carbon atoms in the radical and $R_a$ and $R_b$ are hydrogen, 1 to 4 carbon atom alkyl radicals, or a cycloalkyl radical containing 4 to 8 carbon atoms in the ring, where at least one of $R_a$ and $R_b$ is a cycloalkyl radical, (2) compounds wherein $R_1$ and $R_2$ are methyl radicals and $R_a$ and $R_b$ are hydrogen, 1 to 4 carbon atom alkyl radicals, a phenyl radical, or a benzyl radical, where at least one of $R_a$ and $R_b$ is a phenyl or benzyl radical, and (3) the compound, N,N'-di(oxydiethylene)thiocarbamylsulfenamide, are good fungicides and bactericides. The compositions exhibit a broad range of activity and have good stability during storage.

DETAILED DESCRIPTION

Bactericidal and fungicidal compositions are prepared containing from about 0.01 to about 95% by weight, and more preferredly from about 0.1 to about 5% by weight of the total composition, a thiocarbamylsulfenamide compound of the formula

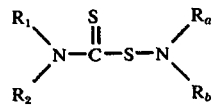

wherein the compound is selected from the group consisting of (1) compounds wherein $R_1$ and $R_2$ are alkyl radicals containing 1 to 3 carbon atoms in the radical and $R_a$ and $R_b$ are hydrogen, 1 to 4 carbon atom alkyl radicals, or a cycloalkyl radical containing 4 to 8 carbon atoms in the ring, where at least one of $R_a$ and $R_b$ is a cycloalkyl radical, (2) compounds wherein $R_1$ and $R_2$ are methyl radicals and $R_a$ and $R_b$ are hydrogen, 1 to 4 carbon atom alkyl radicals, a phenyl radical, or a benzyl radical, where at least one of $R_a$ and $R_b$ is a phenyl or benzyl radical, and (3) the compound, N,N'-di(oxydiethylene)thiocarbamylsulfenamide. The cycloalkyl, phenyl, and benzyl radicals can be further substituted with alkyl radicals containing 1 to 4 carbon atoms. Examples of the compounds are N,N-dimethylthiocarbamyl-N,N'-dicyclobutylsulfenamide, N,N-dimethylthiocarbamyl-N'-methyl-N'-cyclobutylsulfenamide, N,N-dimethylthiocarbamyl-N',N'-dicyclopentylsulfenamide, N,N-dimethylthiocarbamyl-N'-cyclopentylsulfenamide, N,N-dimethylthiocarbamyl-N',N'-dicyclohexylsulfenamide, N,N-dimethylthiocarbamyl-N'-butyl-N'-cyclohexylsulfenamide, N,N-dimethylthiocarbamyl-N'-phenylsulfenamide, N,N-dimethylthiocarbamyl-N',N'-dicycloheptylsulfenamide, N,N-dimethylthiocarbamyl-N'-benzylsulfenamide, N,N-dimethylthiocarbamyl-N',N'-dibenzylsulfenamide, N,N-dimethylthiocarbamyl-N'-ethyl-N'-cycloheptylsulfenamide, N,N-dimethylthiocarbamyl-N',N'-dicyclooctylsulfenamide, N-methyl-N-ethylthiocarbamyl-N',N'-dicyclopentylsulfenamide, N-methyl-N-ethylthiocarbamyl-N'-cyclohexylsulfenamide, N,N-diethylthiocarbamyl-N',N'-dicyclopentylsulfenamide, N,N-diethylthiocarbamyl-N'-isopropyl-N'-cyclopentylsulfenamide, N,N-diethylthiocarbamyl-N',N'-dicyclohexylsulfenamide, N,N-diethylthiocarbamyl-N',N'-dicyclooctylsulfenamide, N,N-diethylthiocarbamyl-N'-methyl-N'-cyclooctylsulfenamide, N-ethyl-N-isopropylthiocarbamyl-N',N'-dicyclohexylsulfenamide, N-ethyl-N-propylthiocarbamyl-N',N'-dicycloheptylsulfenamide, N,N-diisopropylthiocarbamyl-N',N'-dicyclohexylsulfenamide, N-propyl-N-methylthiocarbamyl-N',N'-dicyclopentylsulfenamide, N',N'-di(oxydiethylene)thiocarbamylsulfenamide, and the like.

The more preferred compounds are those wherein (1) $R_1$ and $R_2$ are methyl or ethyl radicals and $R_a$ and $R_b$ are cycloalkyl radicals containing 5 to 7 carbon atoms in the ring, (2) $R_1$ and $R_2$ are methyl radicals and $R_a$ and $R_b$ are hydrogen, phenyl, or benzyl radicals, where at least one of $R_a$ and $R_b$ is a phenyl or benzyl radical, and (3) the compound, N,N'-di(oxydiethylene)thiocarbamylsulfenamide. Examples of the more preferred compounds are N,N-dimethylthiocarbamyl-N',N'-dicyclopentylsulfenamide, N-methyl-N-ethylthiocarbamyl-N',N'-dicyclopentylsulfenamide, N,N-dimethylthiocarbamyl-N'-phenylsulfenamide, N,N-dimethylthiocarbamyl-N',N'-dicyclohexylsulfenamide, N,N-dimethylthiocarbamyl-N',N'-dicycloheptylsulfenamide, N-methyl-N-ethylthiocarbamyl-N',N'-dicycloheptylsulfenamide, N-methyl-N-ethylthiocarbamyl-N',N'-dicyclohexylsulfenamide, N,N-diethylthiocarbamyl-N',N'-dicyclohexylsulfenamide, N,N-dimethylthiocarbamyl-N',N'-dicycloheptylsulfenamide, N,N-diethylthiocarbamyl-N',N'-dicycloheptylsulfenamide, N,N'-di(oxydiethylene) thiocarbamylsulfenamide and the like.

The thiocarbamylsulfenamide compounds can be prepared by various processes. Several processes are disclosed in an article by Smith et al, General Organic Chemistry, Vol. 14 (1949) Page 935. A widely usedd process is to react a dithiocarbamate metal salt with an amine in the presence of an oxidizing agent. Another process is the reaction of a monohaloamine with a tri- or tetrathiocarbamate salt. The monohaloamine is readily obtained by the reaction of a secondary amine with sodium hypochlorite. Yet another route to the preparation of the thiocarbamylsulfenamide compounds is the reaction of an amine and a monohaloamine with carbon disulfide in the presence of a base.

The amines employed have the formula

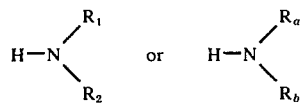

wherein $R_1$, $R_2$, $R_a$ and $R_b$ are defined as above. Examples of the amines are dimethylamine, diethyl amine, dipropyl amine, diisopropyl amine, methylisopropylamine, methylethyl amine, phenyl amine, methylphenyl amine, diphenyl amine, dibenzyl amine, cyclopentyl amine, cyclohexyl amine, methylcyclohexyl amine, dicyclobutyl amine, dicyclohexyl amine, dicycloheptyl amine, dicyclooctyl amine and morpholine.

A particularly useful process for the preparation of the compounds is the reaction of an amine and a chloroamine with carbon disulfide in the presence of a base such as sodium hydroxide, and in a medium of water and a chlorinated solvent such as chloroform or carbon tetrachloride. In this process, the bulkier amine; i.e. the $HNR_aR_b$ amine which contains an aromatic or cycloalkyl radical(s) is directed to the sulfur atom nitrogen position on the thiocarbamylsulfenamide compound. The monochloroamines can be readily prepared by reacting an amine of the formulas above with a chlorinating agent such as sodium hypochlorite, NaOCl. This can be done in situ prior to the reaction of the amine and chloroamine with the carbon disulfide. Temperature of the reaction ranges from about −20° C. to near the boiling point of the reaction mixture, practicably about 80°– 100° C. A more preferred temperature is from about −10° C. to about 50° C. The amine and chloroamine can both be used in a molar excess of the amount of carbon disulfide employed. However, yields of over 70% by weight are readily obtained using about one mole of monochloroamine and one mole of amine to every mole of carbon disulfide present. The thiocarbamylsulfenamide can be isolated by separating out the non-aqueous phase and drying it down to recover the product. The compound can be purified by dissolving it in a suitable solvent such as acetone, diethylether, hexane, toluene, trichloroethane, and the like and precipitating it out by cooling, or by washing the compound using methanol, ethanol, and the like. The thiocarbamylsulfenamides can be characterized by melting point, infra-red spectra, nuclear magnetic resonance (NMR) spectra, and carbon-hydrogen-nitrogen analysis.

The thiocarbamylsulfenamide compounds of this invention have a good range of activity against bacteria and fungi. The compounds exhibit bactericidal activity against, for example, Bacillus subtilis, Staphylococcus aqureus, and Salmonella typhosa; and fungicidal activity against, for example, Aspergillus niger, Trichophyton mentagrophytes and slimes.

The thiocarbamylsulfenamide compounds are mixed with various known carriers and formulary ingredients to prepare the compositions of this invention. The compositions can be simple solutions, dispersions, emulsions or suspensions of the compounds in water or solvents, spray formulations, pastes and gels, dusting powders, or a number of other known forms which are adapted to the end use of the composition. The compositions may be prepared by dissolving or suspending the thiocarbamylsulfenamide in a liquid carrier or by pysically admixing the compound with the ingredients in mixing kettles, Henschel mixers, blenders, Banburys, extruders, ink mills, and the like. Standard mixing techniques are used. The prime requisite is to disperse the compound uniformly throughout the composition.

The compounds are mixed with known fluid carriers as water, solvents, oils and the like or semi-solid and solid carriers and formulary ingredients. In many applications, a concentration of about 0.01 to 95%, usually about 0.1 to 5% by weight of thiocarbamylsulfenamide based on the total weight of thiocarbamylsulfenamide and carrier will be used.

The compositions can be used to control the growth of bacteria and fungi on both organic and inorganic materials by contacting the compositions with the surface of the materials. The end use often determines the level of the thiocarbamylsulfenamide that is used and what carriers and formulary ingredients will be employed.

The thiocarbamylsulfenamide compounds were evaluated as to their activity against organisms, their stability, toxicity, and other properties. A brief description of the testing methods employed follows.

A. Agar Screening Test for Activity.

Test solutions are prepared by dissolving the thiocarbamylsulfenamide in water or a solvent such as acetone. If the compound is not soluble in water or acetone, a suspension of it in water can be prepared by grinding the compound with water and a dispersing agent such as Triton X-100 (alkylaryl polyether alcohol).

A carbon agar such as Mycophil Agar (BBL) or Potato Dextrose Agar is used. The agar is melted in a constant temperature bath and then placed into a sterile Petri dish with the compound test solution. The exact compound concentration in the agar (in parts per million by weight, ppm) is obtained by adding a specific volume of a given concentration of compound in the test solution to a specific weight of the agar. The agar mixture in the dish is mixed and the agar is allowed to harden.

The hardened agar is then inoculated with fungi or bacteria spores by spotting them on the agar using an inoculating needle. Two or three spots are made on each agar sample. The test is run using duplicte agar samples. The inoculated agar samples are then incubated at 95±5% relative humidity for a given time at near optimum temperature for the organism. Results are reported as the lowest ppm of test compound that prevents growth or sporulation of the organism.

B. Penicillin Button Assay Test.

Inoculated agar is prepared by adding organism broth culture (18–24 hours old and transferred at least three times daily) to melted Nutrient Agar. The mixture is stirred to disperse the organism and then transferred to sterile Petri dishes and allowed to harden.

Test solutions are prepared of the thiocarbamylsulfenamide compounds at a given concentration. Penicillin assay buttons, 13 millimeters in diameter, are immersed in the test solutions for 5 minutes. The buttons are then removed, dried, and placed on the hardened inoculated agar. The whole is then incubated at 37° C. for 24 hours at 95±5% relative humidity. Results are reported as the lowest concentration in ppm of thiocarbamylsulfenamide that pevents growth or sporulation of the organism.

C. Toxicity Tests.

The thiocarbamylsulfenamide compounds were also evaluated as to their oral, dermal, and inhalation toxicity. The techniques employed are specified in Section 362.116 of the Regulations for the Enforcement of the Federal Insecticide, Fungicide, and Rodenticide Act, Interpretation 18 (Revised, *Federal Register*, April 4, 1969), or in the Federal Hazardous Substances Act. (Revised, *Federal Register*, September 17, 1964). Acute oral LD50, acute dermal LD50, and acute inhalation LC50 were determined; LD50 being the lethal dose for 50% of the test animals and LC50 being the lethal concentration for 50% of the test animals. Acute oral and acute inhalation tests were run using rats, while acute dermal testing was run using rabbits.

D. Storage Stability Tests.

Thiocarbamylsulfenamide compounds were tested for their stability upon storage at room temperature and after mild thermal aging. The principle test employed consisted of measuring the purity of a sample before and after aging. This was done by titrating a sample solution of the compound using potassium iodide, KI, and sodium thiosulfate, $Na_2S_2O_3$. A 0.5 to 1.0 gram sample of the compound is weighed out and dissolved in 10 milliliters of chloroform. A solution of 2.5 grams of KI in 40 milliliters of water, 10 milliliters of glacial acetic acid, and 20 milliliters of 1 propanol was prepared. The sample solution and the KI solution and then mixed and the whole titrated with a 0.103 Normal solution of $Na_2S_2O_3$ until the color did not change. The calculations are:

$$\left( \frac{\substack{\text{molecular} \\ \text{weight of} \\ \text{pure compound}} \times \substack{\text{milliliters} \\ \text{of } Na_2S_2O_3 \\ \text{solution used}} \times \substack{\text{normality} \\ \text{of } Na_2S_2O_3 \\ \text{solution}}}{\text{weight of sample} \times 1000} \right) \times 100$$

The value obtained is the percent by weight of the sample that is the desired thiocarbamylsulfenamide. The titration is run on the sample before and after aging. The change in purity of the compound indicates its decomposition upon storage. Little or no decrease in purity shows that the thiocarbamylsulfenamide compounds have good storage stability.

In addition to the titration test, other tests were run. The melting point of the compound was measured both before and after aging. Little or no change in melting point indicates good storage stability. Further, observations were made upon the appearance and odor of the compounds before and after aging.

The following Examples serve to more fully illustrate the invention.

EXAMPLE I

N,N-dimethylthiocarbamyl-N',N'-dicyclohexylsulfenamide was prepared. 100 milliliters of carbon tetrachloride, 39.6 grams of a solution of dimethylamine at 25% by weight in water (0.22 mole) and 36.2 grams (0.2 mole) of dicyclohexylamine were placed in a reactor vessel and the mixture cooled to 10° C. 114 milliliters of a solution of NaOCl at 14% by weight in water (0.23 mole) was added and the mixture stirred for 15 minutes at 10° to 15° C. 200 milliliters of water containing 25 grams of $NaHCO_3$ and 11 grams of $Na_2CO_3$ was then added as a buffer solution. The mixture was warmed to 20° C. and 15.2 grams (0.2 mole) of carbon disulfide was added while stirring. The mix was stirred for 40 minutes at a temperature of about 32°–35° C. The mixture was allowed to settle and the non-aqueous phase separated out and filtered. The carbon tetrachloride was then evaporated off, leaving 61 grams of a thick liquid. 150 milliliters of methanol was added and the liquid first dissolved, then a solid precipitated out. The methanol slurry was cooled to −10° C. and filtered. The solids isolated were dried, and 44.1 grams of a white crystalline solid having a melting point of 85°–87° C. was obtained. The yield was 77% by weight based upon the weight of carbon disulfide used. The N,N-dimethylthiocarbamyl-N',N'-dicyclohexylsulfenamide was identified by its Infra-red spectrum. The calculated element weights for the formula $C_{15}H_{28}N_2S_2$ were 9.32% nitrogen, 60.0% carbon, and 9.32% hydrogen. Analytical values were 9.34% nitrogen, 59.8% carbon, and 9.60% hydrogen respectively.

Following the procedure above, N,N-diethylthiocarbamyl-N',N'-dicyclohexylsulfenamide was prepared. Diethylamine was used in place of dimethylamine. The compound is a liquid at room temperature.

Similarly, dibutylamine and dieicosylamine were used in place of dimethylamine. The compounds made were N,N-dibutylthiocarbamyl-N',N'-dicyclohexylsulfenamide and N,N-dieicosylthiocarbamyl-N',N'-dicyclohexylsulfenamide.

EXAMPLE II

N-oxydiethylenethiocarbamyl-N',N'-dicyclohexylsulfenamide was pepared. 100 milliliters of chloroform, 17.4 grams (0.2 mole) of morpholine, and 36.2 grams (0.2 mole) of dicyclohexylamine were placed in a reactor vessel, cooled to 0° C., and then 110 grams of a solution of NaOCl at 13% by weight in water (0.2 mole) was added. The mixture was stirred for 10 minutes and 15.2 grams (0.2 mole) of carbon disulfide was added. An additional 100 milliliters of chloroform was added. After 20 more minutes of stirring at a temperature of about 32±2° C., the mixture was allowed to settle. The non-aqueous phase was separated out, and the chloroform evaporated off. A light yellow solid was obtained. The solid was slurried in 100 milliliters of methanol, cooled to −10° C., filtered, and the filtrate washed with 25 milliliters of methanol to yield 51.1 grams of a white crystalline solid. Water was added to the methanol solution which precipitated out an additional 1.5 grams of solid. Total weight obtained was 52.6 grams, reflecting a yield of 77% of theoretical based on the amount of carbon disulfide employed. The IR spectrum and carbon-hydrogennitrogen analysis were consistent with the desired compound. Calculated weight percent for the formula $C_{17}H_{30}N_2S_2O_2$ were 59.6% carbon, 8.2% nitrogen, and 8.8% hydrogen, and analytical values were 59.5% carbon, 8.1% nitrogen, and 9.1% hydrogen. The compound had a melting point of 179°–181° C.

Following the procedure given above, hexamethyleneamine was reacted with dicyclohexylchloroamine and carbon disulfide in the presence of NaOH to yield N-hexamethylenethiocarbamyl-N',N'-dicyclohexylsulfenamide. The compound, obtained in a 40% by weight yield, had a melting point of 88°–89° C.

EXAMPLE III

N-oxydiethylenethiocarbamyl-N'-oxydiethylenesulfenamide was prepared by reacting about 0.2 mole of morpholine and about 0.2 mole of N-chloromorpholine chloride with 0.2 mole of carbon disulfide in the presence of about 0.2 mole of NaOH and in a medium of water and chloroform. 34.8 grams (0.4 mole) of morpholine was added to 50 milliliters of chloroform and the solution cooled to 0° C. 110 grams of a solution of NaOCl at 13% by weight in water (0.2 mole) was added and the mixture stirred for 10 minutes at a temperature of about 10° C. 15.2 grams (0.2 mole) of carbon disulfide was then added and the mix stirred for 10 minutes at 10°±5° C. The mixture became thick and an additional 50 milliliters of chloroform was added. After 15 minutes of stirring, the mixture was allowed to settle and the non-aqueous phase was separated out. The chloroform was evaporated off under reduced pressure. The pale yellow crystals obtained were slurried in methanol, filtered out and dried. The yield of compound was 45.2 grams, 92% by weight of theoretical. The compound was identified by its IR spectrum, and it had a melting point of 128°–134° C.

When 0.2 mole of dimethylamine was used in place of 0.2 mole of morpholine in the above procedure, the product obtained was N,N-dimethylthiocarbamyl-N′-oxydiethylenesulfenamide. The compound obtained in 17% by weight yield had a melting point of 75°–78° C.

EXAMPLE IV

N,N-dimethylthiocarbamyl-N′,N′-dimethylsulfenamide was prepared by reacting about 0.22 mole of dimethylamine and about 0.22 mole of dimethylchloroamine with 0.2 mole of carbon disulfide in the presence of about 0.32 mole of NaOH and in a mixture of carbon tetrachloride and water. The dimethylchloroamine was prepared in situ prior to use. 150 milliliters of carbon tetrachloride was added to a reactor vessel equipped for agitation. 79.2 grams of a solution of dimethylamine at 25% by weight in water (0.44 mole) was added and the mixture cooled to 10° C. A solution of 14% by weight NaOCl in water (0.22 mole) was added and the mix agitated for 15 minutes at 10° C. The reaction mixture contained about 0.22 mole of dimethylamine, about 0.22 mole of dimethylchloroamine, and about 0.22 mole of NaOH by-product. To this reaction mixture, 4.0 grams of NaOH (0.1 mole) and 15.2 grams (0.2 mole) of carbon disulfide was added. The mixture was stirred for 15 minutes at 6° C. to 12° C. and then allowed to settle. The pH of the aqueous phase was about 10. The non-aqueous phase was separated out, filtered, and the carbon tetrachloride evaporated off under reduced pressure. A white crystalline solid, having a melting point of 49° C., was obtained in the amount of 23.7 grams, reflecting a yield of 72% by weight. The compound was identified by its IR spectrum.

Following the procedure given, N,N-dimethylthiocarbamyl-N′,N′-diisopropylsulfenamide was prepared by reacting dimethylamine with diisopropylchloroamine and carbon disulfide. The compound was obtained in a 50% yield by weight, and had a melting point of 52°–53° C.

EXAMPLE V

Thiocarbamylsulfenamide compounds prepared in Examples I to IV were evaluated for their activity against organisms. The compounds are presented in the following table.

| Compound | Name | Melting Point °C. |
|---|---|---|
| A | N,N-dimethylthiocarbamyl-N′,N′-dicyclohexylsulfenamide | 85–87 |
| B | N,N-diethylthiocarbamyl-N′,N′-dicyclohexylsulfenamide | liquid |
| C | N,N-dibutylthiocarbamyl-N′,N′-dicyclohexylsulfenamide | — |
| D | N,N-dieicosylthiocarbamyl-N′,N′-dicyclohexylsulfenamide | — |
| E | N-oxydiethylenethiocarbamyl-N′,N′-dicyclohexylsulfenamide | 179–181 |
| F | N-hexamethylenethiocarbamyl-N′,N′-dicyclohexylsulfenamide | 88–89 |
| G | N-oxydiethylenethiocarbamyl-N′-oxydiethylenesulfenamide | 128–134 |

In addition to the prepared compounds, two additional compounds were evaluated. The compounds are (H) N,N-dimethylthiocarbamyl-N′-phenylsulfenamide and (I) N,N-diethylthiocarbamyl-N′-phenylsulfenamide.

The nine compounds were evaluated for their activity against various infectious organisms. The Agar Screening Test and/or the Penicillin Button Assay Test were employed. The organisms tested against were (a) *Asperigillus niger*, a fungus, and the bacteria, (b) *Bacillus subtilis*, (c) *Staphylococcus aureus*, and (d) *Salmonella typhosa*. The results of the testing are reported as the lowest concentration of the thiocarbamylsulfenamide compound in parts per million by weight (ppm) based upon the weight of the agar that prevents growth or sporulation of the organism. A low value indicates a high degree of activity against the organism. Data is as follows:

| Compound | (a) | (b) | (c) | (d) |
|---|---|---|---|---|
| A | 300 | 10 | 20 | 50 |
| B | over 1000 | 50 | 20 | 100 |
| C | over 1000 | over 10000 | over 10000 | over 10000 |
| D | over 1000 | over 10,000 | over 10,000 | over 10,000 |
| E | over 1000 | 10,000 | 10,000 | over 10,000 |
| F | over 1000 | over 10,000 | over 10,000 | over 10,000 |
| G | 1000 | 50 | 50 | 100 |
| H | 300 | 20 | 50 | 50 |
| I | over 1000 | 10,000 | 1000 | 10,000 |

Solutions of 0.001 to 1.0% were used. Compounds A, B, G and H are in the scope of this invention. Compounds C, D, E, F and I are outside of the scope of the present invention. The activity of a thiocarbamylsulfenamide compound is quite selective, as the data shows. For example, compounds A and B having dimethyl and diethyl radicals in the N,N positions have good activity, while compounds C and D containing N,N-dialkyl radicals where the alkyl radical has more than 3 carbon atoms show no activity. Compound G which is in the scope of the invention had good activity, while compound E which shares groups common to both compounds G and A has almost no activity. Compound H having dimethyl radicals in the N,N positions shows good activity, while compound I having two ethyl radicals shows very little activity.

EXAMPLE VI

Two of the compounds evaluated for their activity against organisms (compounds A and G respectively in Example V) were tested for their toxicity following the procedure previously given in the specification. Test results are as follows:

| Compound | Acute Oral LD50[1] | Acute Dermal LD50[1] | Acute Inhalation LC50[2] |
|---|---|---|---|
| A | 1.1 | over 10 | 78 |
| G | 5.1 | over 10 | 164 |

[1] -grams per kilogram of body weight
[2] -milligrams per liter of air

The data indicate that both Compound A (N,N-dimethylthiocarbamyl-N',N'-dicyclohexylsulfenamide) and Compound B (N-oxydiethylenethiocarbamyl-N'-oxydiethylenesulfenamide) are non-toxic by dermal absorption and inhalation. Classification as to toxicity is according to federal regulations.

EXAMPLE VII

The thiocarbamylsulfenamides of the invention have good storage stability. This is important if the compounds are going to be used in disinfectant solutions, and stored and marked without a significant loss in activity against organisms. Other known thiocarbamylsulfenamide compounds do not have good storage stability. The compounds were aged in an air oven, while in closed bottles. The test methods used were previously described. The data obtained is as follows:

| Compound | A | J | A | G | K |
|---|---|---|---|---|---|
| Aging conditions | | | | | |
| Temperature, °C. | 50 | 50 | 80 | 80 | 80 |
| Time | 10 days | 10 days | 16 hrs. | 16 hrs. | 16 hrs. |
| Percent Purity | | | | | |
| Before aging | 99 | 96 | 100 | 98 | 93 |
| After aging | 99 | 77 | 97 | 98 | 89 |
| Melting point, °C. | | | | | |
| Before aging | 85–87 | 49–51 | 84–85 | 136–139 | 56–57 |
| After aging | 85–87 | 34–39 | 83–85 | 135–139 | 53–54 |
| Color | | | | | |
| Before aging | white | off-white | white | white | white |
| After aging | off-white | yellow | white | off-white | light yellow |
| Amine odor | | | | | |
| Before aging | slight | slight | slight | slight | mild |
| After aging | slight | strong | slight | slight | strong |

The compounds are identified as: (A) N,N-dimethylthiocarbamyl-N',N'-dicyclohexylsulfenamide, prepared in Example I, (G) N-oxydiethylenethiocarbamyl-N'-oxydiethylenesulfenamide, prepared in Example III, (J) N,N-dimethylthiocarbamyl-N',N'-dimethylsulfenamide, prepared in Example IV, and (K) N,N-dimethylthiocarbamyl-N',N'-diisopropylsulfenamide, prepared in Example IV. Compounds A and G are within the scope of the present invention. Both compounds show good activity against organisms (see Example V). Compounds J and K are thiocarbamylsulfenamides known to have activity against organisms (see U.S. Pat. No. 2,692,862). The data clearly shows that the thiocarbamylsulfenamides of the present invention are more stable, and will not rapidly decompose during processing operations and formulation or during storage.

We claim:

1. A composition having bactericidal and fungicidal properties containing (A) as an active ingredient from about 0.01 percent to about 95 percent by weight based upon the weight of the composition of a thiocarbamylsulfenamide

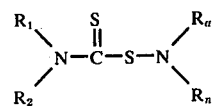

selected from the group consisting of N,N-dimethylthiocarbamyl-N',N'-dicyclohexylsulfenamide and N,N-diethylthiocarbamyl-N',N'-dicyclohexylsulfenamide, and (B) water as a carrier.

2. A composition of claim 1 wherein the said thiocarbamylsulfenamide compound is present in a bactericidally and fungicidally effective amount of from about 0.1 percent to about 3 percent by weight of the composition.

3. A composition of claim 2 wherein the thiocarbamylsulfenamide compound is N,N-dimethylthiocarbamyl-N',N'-dicyclohexylsulfenamide.

4. A composition of claim 2 wherein the thiocarbamylsulfenamide compound is N,N-diethylthiocarbamyl-N',N'-dicyclohexylsulfenamide.

* * * * *

UNITED STATES PATENT OFFICE
CERTIFICATE OF CORRECTION

PATENT NO. : 4,006,251

DATED : February 1, 1977

INVENTOR(S) : Ray D. Taylor & Robert A. Krueger

It is certified that error appears in the above--identified patent and that said Letters Patent are hereby corrected as shown below:

Column 10, in Claim 1, at line 14, delete the number "21"; at line 15, before the word from, add the words --a bactericidally and fungicidally effective amount of--; at line 20, delete the formula

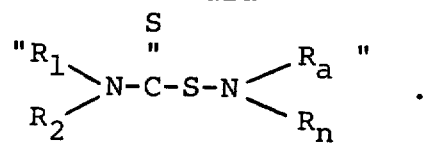

Signed and Sealed this

Thirty-first Day of January 1978

[SEAL]

Attest:

RUTH C. MASON
Attesting Officer

LUTRELLE F. PARKER
Acting Commissioner of Patents and Trademarks